United States Patent [19]

Morpeth

[11] Patent Number: 5,451,577
[45] Date of Patent: Sep. 19, 1995

[54] ANTIMICROBIAL COMPOSITION AND USE

[75] Inventor: Fraser F. Morpeth, Bury, England

[73] Assignee: Zeneca Limited, London, England

[21] Appl. No.: 115,798

[22] Filed: Sep. 3, 1993

Related U.S. Application Data

[63] Continuation of Ser. No. 805,408, Dec. 10, 1991, abandoned.

[30] Foreign Application Priority Data

Dec. 20, 1990 [GB] United Kingdom ............... 9027614

[51] Int. Cl.$^6$ ................. C07D 401/02; C07F 3/06; A61K 31/44; A01N 43/40
[52] U.S. Cl. .................... 514/186; 514/188; 546/6; 546/270; 252/106; 252/107
[58] Field of Search ............... 514/188, 186; 252/106, 252/107

[56] References Cited

FOREIGN PATENT DOCUMENTS

2208474 4/1989 United Kingdom ............... 546/261
2230190 10/1990 United Kingdom ............... 546/261

OTHER PUBLICATIONS

Mar. Advanced Organic Chemistry, Second Edition, p. 1132, McGraw Hill Pub. (1977).
Noller, Chemistry Of Organic Compounds, Second Edition, pp. 275, 280, Saunders Pub. 1957.
Reid, Organic Chemistry Of Bivalent, Sulfur, vol. III, p. 376 Chem. Publishing Co., 1960.

*Primary Examiner*—Alan L. Rotman
*Attorney, Agent, or Firm*—Cushman Darby & Cushman

[57] ABSTRACT

A composition which contains a 4,5-polymethylene-4-isothiazolin-3-one and a salt or complex of 2-mercaptopyridine-1-oxide with a metal which is at least divalent. The salt or complex is typically zinc 2-thiopyridine-1-oxide. The compositions exhibit anti-microbial activity and certain combinations of isothiazolinones together with zinc 2-thiopyridine-1-oxide are surprisingly effective against both bacteria and fungi.

13 Claims, No Drawings

ANTIMICROBIAL COMPOSITION AND USE

This is a continuation of application Ser. No. 07/805,408, filed on Dec. 10, 1991, which was abandoned upon the filing hereof.

The present invention relates to compositions which have antimicrobial activity and are useful as industrial biocides.

Materials having antimicrobial activity can be used as industrial biocides to prevent industrial spoilage, in particular that caused by bacteria and fungi. Industrial biocides find application in the preservation of paints, latices, adhesives, leather, wood, metal working fluids and cooling water.

One class of compound which has antimicrobial activity and can be used as an industrial biocide is based on the isothiazolinone structure. There are many disclosures of isothiazolinone derivatives which are stated to have useful biocidal properties. U.S. Pat. No. 3,761,488 discloses isothiazolinone derivatives in which alkyl, alkenyl, alkynyl, cycloalkyl, aralkyl or aryl groups, which may optionally be substituted, are attached to the nitrogen atom and the 4 and 5 positions are unsubstituted or are substituted with halogen or lower alkyl groups. U.S. Pat. No. 4,165,318 discloses a solution of an isothiazolin-3-one in a polar organic solvent, wherein the solution also contains a stabilising amount of formaldehyde. British Patent Specification 2087388 discloses 4,5-polymethylene-4-isothiazolin-3-ones in which the polymethylene chain has three or four carbon atoms.

A further class of compounds which have found a use as industrial biocides are the metal salts or complexes of 2-mercaptopyridine-1-oxide. Such compounds have been disclosed in, for example, U.S. Pat. No. 2,686,786, 2,758,116 and 2,809,971.

Compounds and compositions of the foregoing types, and related compounds of the same general type, are effective to a varying degree, depending on the particular compound or composition, against a range of bacteria and/or fungi. However, to reduce the cost of using these compounds it is desirable to improve their effectiveness as antimicrobial materials.

Compositions have been proposed which contain more than one compound which has antimicrobial properties. In general such compositions show an aggregate of the properties of the compounds present in the composition. Typically such compositions contain one compound which exhibits useful antibacterial properties together with a different compound which exhibits useful antifungal properties.

We have now found that certain compositions possess surprisingly useful antimicrobial especially anti-bacterial properties.

Thus, according to the present invention there is provided a composition which comprises
   (a) at least one 4,5-polymethylene-4-isothiazolin-3-one or a derivative thereof, and
   (b) at least one salt or complex of 2-mercaptopyridine-1-oxide with a metal which is at least divalent.

The 4,5 polymethylene-4-isothiazolin-3-one derivative which is component a) of the composition is typically a compound of the general formula I.

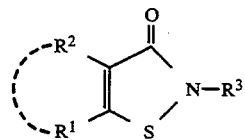

wherein:

$R^1$ and $R^2$ taken together represent a polymethylene chain, having 3 or 4 carbon atoms or a polymethylene chain having 3 or 4 carbon atoms substituted by at least one lower alkyl radical having from 1 to 4 carbon atoms;

$R^3$ represents hydrogen; a linear or branched alkyl group having from 1 to 12 carbon atoms; a linear or branched alkyl group having from 1 to 3 carbon atoms substituted by one or more hydroxyl groups; an alkenyl group having from 3 to 6 carbon atoms; a radical of the formula

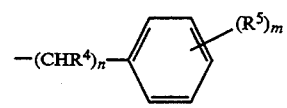

wherein:

n is 0 or 1;

m is 1 or 2;

$R^4$ represents hydrogen or a lower alkyl group; and $R^5$ represents hydrogen, lower alkyl, nitro, trifluoromethyl or halogen, preferably chlorine, bromine or iodine; cyclo alkyl having from 3 to 6 carbon atoms; and a radical of formula

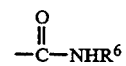

wherein $R^6$ represents hydrogen, linear or branched alkyl having from 1 to 12 carbon atoms or a radical of the formula

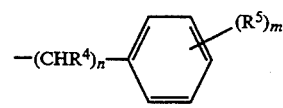

as defined above, and their salts or complex with a mineral or organic acid, or with a base.

In a preferred embodiment of the invention the 4,5-polymethylene-4-isothiazolin-3-one can be represented by the general formula II

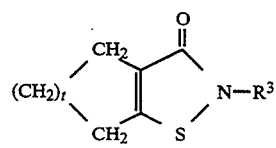

wherein t is 1 or 2 and $R^3$ is as defined above. These compounds are, thus, derivatives of 4,5-trimethylene or 4,5-tetramethylene-4-isothiazolin-3-ones.

$R^3$, in formulae I and II, may be a linear or branched alkyl group, such as methyl, ethyl, propyl, isopropyl, butyl, isobutyl, tert-butyl, hexyl, octyl or dodecyl.

When $R^3$ represents alkyl substituted by one or more hydroxyl groups, this includes, for instance, hydroxymethyl, 2-hydroxyethyl, 2-hydroxypropyl and 1,2 dihydroxy propyl.

As an example of alkenyl as represented by $R^3$, there may be mentioned allyl.

When $R^3$ represents a radical of formula

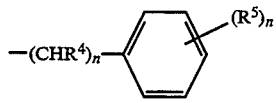

this can be, for example, phenyl, chlorophenyl, 2,4-dichlorophenyl, benzyl, 4-chlorobenzyl or 2,4-dichlorobenzyl.

When $R^3$ represents cycloalkyl having from 3 to 6 carbon atoms, this can be, for example, cyclopropyl, cyclobutyl, cyclopentyl or cyclohexyl.

When $R^3$ represents a radical of formula

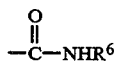

it can be carbomoyl, N-methyl carbamoyl, N-ethylcarbamoyl, N-isopropyl carbamoyl, N-propyl carbamoyl, N-phenyl carbamoyl, N-cyclohexyl carbamoyl, N-butyl carbamoyl or N-octyl carbamoyl.

Finally, when the compound of formula I forms a complex with a base, $R^3$ is a cation. This cation may have a valency of more than one, but is particularly a monovalent cation such as an alkali metal, an amine or quaternary ammonium cation.

The salts formed between the compound of formula I and a mineral or organic acid, and the complexes formed between the compound of formula I and a base are generally water soluble and hence can be used in aqueous solution.

The term lower alkyl represented by $R^4$ above includes linear or branched alkyl chains containing up to 4 carbon atoms such as methyl, ethyl, isopropyl, butyl and tertiary butyl.

As specific examples of compounds which may be used as component (a) of the composition of the present invention, there may be mentioned 2-methyl-4,5-trimethylene isothiazolin-3-one (formula II, in which t is 1 and $R^3$ is methyl), and 4,5-trimethylene isothiazolin-3-one (formula II, in which t is 1 and $R^3$ is hydrogen).

Component (b) of the composition of the present invention is at least one salt or complex of 2-mercaptopyridine-1-oxide with a metal (M) which is at least divalent. The metal M is a metal of Groups IIIA to VA or IB to VIIB of the Periodic Table provided the metal is in at least the divalent state. All references herein to the Periodic Table are to the Periodic Table according to Mendeleeff, as set out on the inside rear cover of "Handbook of Chemistry and Physics" 49th Edition (1968-1969) published by The Chemical Rubber Co, Cleveland, Ohio, USA. We have obtained compounds having useful properties when the metal is a metal of Group IIB, for example zinc.

The salt or complex which is component (b) of the composition of the present invention can be prepared using known techniques for the preparation of a metal salt or complex. Conveniently the metal complex is prepared by the reaction of a salt of the metal with 2-mercaptopyridine-1oxide.

The salt of the metal M is preferably used as a solution in a suitable solvent. Thus, the salt may be an acetate such as zinc acetate which is dissolved in an alcohol, for example methanol.

The reaction is conveniently effected by mixing together solutions, in the same solvent, of the salt of the metal and the 2-mercaptopyridine-1oxide. The solutions can be mixed together without heating the mixture. However, whilst the reaction can be effected at essentially ambient temperature (15°-20° C.), higher or lower temperatures may be used, for example from 0° C. up to 100° C., although it is generally not preferred to use a temperature in excess of 50° C.

The reaction is preferably effected in a liquid which is a solvent for the reactants but a non-solvent for the metal complex obtained. The metal complex is typically a solid and is formed as a precipitate during the reaction. The solid is readily separated from the reaction mixture, for example by filtration. The solid is then washed to remove impurities, for example using water, the solvent used for the preparation or both in sequence and/or as a mixture.

The reaction is conveniently effected by mixing together solutions of the two reactants and stirring to effect reaction. If the metal complex separates as a solid, stirring of the reaction mixture is continued from 0.1 up to 10 hours, for example 0.5 up to 2 hours. Stirring is then terminated and the solid is separated, conveniently by filtration but other techniques such as allowing the solid to settle and removing the supernatant liquid phase may also be used.

The metal salt and 2-mercaptopyridine-1-oxide are conveniently reacted together in essentially the stoichiometric quantities required to obtain the desired metal salt or complex. Thus, the molar ratio of 2-mercaptopyridine-1-oxide to the metal salt is typically 0.9x:1 to 1.1x:1 and especially is 0.95x:1 to 1.05x:1, where x is the molar ratio of pyridine oxide to metal in the salt or complex and typically corresponds to the valency of the metal.

As a particular embodiment of the present invention there is provided a composition comprising 2-methyl-4,5-trimethylene-4-isothiazoline-3-one and a 2:1 complex of 2-thiopyridine-1-oxide and zinc.

In various types of applications, it is frequently necessary or convenient to formulate the 4,5-polymethylene-4-isothiazolin-3-one in solution, especially using water or polar organic solvents such as alcohols.

When the 4,5-polymethylene-4-isothiazolin-3-ones are used in aqueous solution, their solubility may be improved by forming their salts with strong organic and/or inorganic acids such as hydrochloric, sulphuric, succinic and citric acids.

The relative proportions of the components of the composition can vary, and the composition typically contains components (a) and (b) in the relative proportions by weight of from 100:1 to 1:100. In general the composition contains components (a) and (b) in the proportions by weight of from 50:1 to 1:50, especially from 10:1 to 1:10. A composition which has been found to have useful antimicrobial properties contains components (a) and (b) in the weight proportions of 1:2.

The compositions of the present invention have antimicrobial properties. We have found that compositions in accordance with the present invention are active against both bacteria and fungi. Furthermore, compositions in accordance with the present invention are such that the sum of the fractional inhibitory concentration (FIC) for all the components of the composition is less than one and, with preferred compositions is less than 0.9. Especially preferred compositions are those in which the sum of the FIC for all the components of the composition is not more than 0.7. The FIC is the ratio of the concentration of an individual component to the minimum inhibitory concentration of that component. It will be appreciated that if the value of the sum of the FIC for all the components of the composition is less than one, the composition is synergistic, the extent of synergy being indicated by the amount by which the sum of the FIC is below one. We have found that some compositions in accordance with the present invention are such that the sum of the FIC is less than 0.7.

The compositions of the present invention have antimicrobial properties and are suitable for use as industrial biocides. They exhibit good wet state preservation and hence may be used as a cutting fluid preservative and also in cooling water applications. They may also be used in paper mill liquors. Furthermore, the composition may be used to preserve industrially important formulations, especially aqueous based formulations, which are used for coloration, such as dyuestuffs and printing inks. They may also be used in the agrochemical industries to preserve formulations such as herbicide and pesticide flowables.

Still further important applications of the compositions of the present invention include their use in hydrocarbon fluids such as diesel fuels. They may also be incorporated into adhesives in order to inhibit microbial spoilage.

The preservation of wood and leather is yet another important application of the compositions.

Especially important is the use of the composition of the present invention in paints, particularly in aqueous based latices.

A particularly preferred use of the compositions of the present invention is the preservation of polyvinyl acrylate and particularly acrylic latices, especially those whose pH is above 7, and especially those containing ammonia or amines.

The materials which are component (a) and component (b) of the composition of the present invention are soluble in many polar solvents, although the solubility is dependent on the nature of the particular compounds which are present in the composition. However, many of the compounds are soluble in water, alcohols, ethers, ketones and other polar solvents or mixtures thereof.

The compositions of the present invention may be used alone as an antimicrobial material but may also be used in, or on, a suitable carrier material.

Thus, as a further aspect of the present invention there is provided a biocide composition comprising a carrier and an effective amount of a composition of components (a) and (b) in accordance with the invention.

The carrier is typically a material which shows little, if any, antimicrobial activity and may be, or include, a material which is susceptible to the growth of microorganisms, particularly bacteria. The carrier is preferably a liquid medium and the biocide composition may be a solution, suspension or emulsion of the composition of components (a) and (b) in a liquid carrier. The carrier may be water, in which one or both of components (a) and (b) are soluble, or may be a liquid such as-acetic acid, N,N-dimethyl-formamide, propylene glycol, dimethyl sulphoxide or N-methyl-2-pyrrolidone in which at least one, and preferably both, of components (a) and (b) are soluble. Alternatively, a mixture of liquids may be used, one being a solvent for component (a) and component (b) and the other being a non-solvent for both components, and using such a mixture the composition typically comprises an emulsion or droplets of a solution of components (a) and (b) in the solvent therefor dispersed in the non-solvent. If a suspension or emulsion is used, this conveniently contains a surface active agent which is effective to maintain the non-continuous phase as a suspension or emulsion. Any surface active agent known for use in biocide compositions may be used in such a system, for example alkylene oxide adducts of fatty alcohols, alkyl phenols and amines such as ethylene diamine.

Whereas it is advantageous in using the composition of the present invention to add component (a) and component (b) simultaneously, it will be appreciated that in certain circumstances it may be beneficial to add component (a) and component (b) sequentially.

The amount of the composition which is present in the biocide composition may be just sufficient to have an antimicrobial effect or the composition may be present in a substantially greater proportion. It will be appreciated that the biocide composition may be provided as a concentrated solution which is subsequently diluted for use as an antimicrobial material. The higher concentrations of the biocide composition are useful, for example, in the bulk transportation of the composition. Thus, the amount of the composition of components (a) and (b) which is present in the biocide composition is typically in the range from 0.0001% up to 30% by weight of the biocide composition.

The composition of the present invention is especially effective in providing anti-microbial activity. Thus, the compositions can be used for the treatment of various media to inhibit the growth of micro-organisms.

As a further aspect of the present invention there is provided a method for inhibiting the growth of microorganisms on, or in, a medium which comprises treating the medium with a composition of components (a) and (b) as hereinbefore defined.

The composition can be used in conditions in which micro-organisms grow and cause problems. Systems in which micro-organisms cause problems include liquid, particularly aqueous, systems such as cooling water liquors, paper mill liquors, metal working fluids, geological drilling lubricants, cosmetics, polymer emulsions and surface coating compositions such as paints, varnishes and lacquers and also solid materials such as paper, wood, leather and plastics materials such as PVC and polyurethane. The composition of the present invention can be included in such materials to provide an anti-microbial effect. The amount of the composition is typically in the range from 0.0001 up to 10%, preferably 0.001 up to 5% and especially 0.002 to 1% by weight of the composition relative to the system to which it is added. In many cases, microbial inhibition has been obtained with between 0.005% and 0.1% by weight of the composition.

Components (a) and (b) of the composition of the present invention may be the only antimicrobial compounds or may be used together with further compounds having antimicrobial characteristics. The composition may contain more than one compound which is component (a) together with one or more compounds which is component (b). Alternatively, a composition of components (a) and (b) in accordance with the present invention may be used together with one or more known antimicrobial compounds. The use of a mixture of anti-microbial compounds can provide a composition having a broader anti-microbial spectrum and hence one which is more generally effective than the components thereof. The known antimicrobial may be one possessing anti-bacterial, anti-fungal, anti-algal or other antimicrobial characteristic. The mixture of the composition of the present invention with other antimicrobial compounds typically contains from 1 to 99% by weight, relative to the weight of total antimicrobially active compounds, of the composition of components (a) and (b), and particularly from 40 to 60% by weight of the composition of components (a) and (b).

As examples of known antimicrobial compounds which may be used, together with the composition of the present invention, there may be mentioned quaternary ammonium compounds such as diethyldodecylbenzyl ammonium chloride; dimethyloctadecyl-(dimethylbenzyl)ammonium chloride; dimethyldidecylammonium chloride; dimethyldidodecylammonium chloride; trimethy-tetradecylammonium chloride; benzyldimethyl($C_{12}$–$C_{18}$ alkyl) ammonium chloride; dichlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecyl-bis(beta-hydroxyethyl)ammonium chloride; dodecyl-benzyltrimethylammonium chloride; benzyldimethyl($C_{12}$–$C_{18}$ alkyl) ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamantane chloride; urea derivatives such as 1,3-bis(hydroxymethyl)-5,5-dimethylhydantoin; bis(hydroxymethyl)urea; tetrakis(hydroxy-methyl)acetylene diurea; 1-(hydroxymethyl)-5,5-dimethylhydantoin and imidazolidinyl urea; amino compounds such as 1,3-bis(2-ethyl-hexyl)-5-methyl-5-aminohexahydropyrimidine; hexamethylene tetra amine; 1,3-bis(4-aminophenoxy)propane; and 2-[(hydroxymethyl)amino] ethanol; imidazole derivatives such as 1[2-(2,4-dichloro-phenyl)-2-(2-propenyloxy)ethyl]-1H-imidazole; 2-(methoxycarbonyl-amino)-benzimidazole; nitrile compounds such as 2-bromo-2-bromomethylglutaronitrile, 2-chloro-2-chloromethylglutaronitrile and 2,4,5,6-tetrachloroisophthalodinitrile; thiocyanate derivatives such as methylene bis thiocyanate; tin compounds or complexes such as tributyltinoxide, chloride, naphthoate, benzoate or 2-hydroxybenzoate; other isothiazolin-3-one derivatives such as 2-methylisothiazolin-3-one, 5-chloro-2-methylisothiazolin-3-one, benzisothiazolin-3-one, and 2-methylbenzisothiazolin-3-one; thiazole derivatives such as 2-(thiocyanomethylthio)-benzthiazole; and mercaptobenzthiazole; nitro compounds such as tris(hydroxymethyl)-nitromethane; 5-bromo-5-nitro-1,3dioxane and 2-bromo-2-nitropropane-1,3-diol; iodine compounds such as iodopropynyl butyl carbamate and tri-iodo allyl alcohol; aldehydes and derivatives such as gluteraldehyde (pentanedial) p-chlorophenyl-3-iodopropargyl formaldehyde and glyoxal; amides such as chloracetamide; N,N-bis(hydroxymethyl)chloracetamide; N-hydroxymethyl-chloracetamide and dithio-2,2-bis(benzmethyl amide); guanidine derivatives such as poly hexamethylene biguanide and 1,6-hexamethylene-bis[5-(4-chlorophenyl) biguanide]; thiones such as 3,5-dimethyl-tetrahydro-1,3,5-2-thiodiazine-2-thione; triazine derivatives such as hexahydrotriazine and 1,3,5-tri-(hydroxyethyl)- 1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichloro- phenoxy)phenol; thio-bis(4-chlorophenol) and 2-phenylphenol; sulphone derivatives such as diiodomethyl-paratolyl sulphone, 2,3,5,6-tetrachloro-4-(methylsulphonyl) pyridine and hexachlorodimethyl sulphone.

Further aspects of the present invention are described in the following illustrative examples.

In the following examples, compositions in accordance with the present invention were subjected to evaluation of the antimicrobial properties of the compositions. The evaluation was effected, under sterile conditions throughout, as follows:

In the microbiological evaluation, various compositions were tested for anti-microbial activity against bacteria. The bacterium used was Pseudomonas aeruginosa.

Microbiological evaluation

The materials, or mixture of materials, to be tested were added to a nutrient broth in amounts to give a desired concentration of the added material. The added materials were added at concentrations from zero to above the minimum inhibitory concentration of the particular material. In the mixtures, the concentrations of each material were varied in a systematic fashion to give a matrix of mixtures of different relative proportions and different total concentrations.

The effect on the inhibition of growth of bacteria was investigated by inoculating each sample of broth with sufficient of the test bacterium to give about $10^5$ cells $cm^{-3}$. The mixture was incubated at 30° C. for 48 hours. At the end of the test period the presence of turbidity in the broth indicated that growth of the test bacterium had occurred. A lack of turbidity was indicative that no growth had occurred. The results were used to draw an isobologram from which the sum of the fractional inhibitory concentration for a mixture can be determined.

EXAMPLE 1

The microbiological evaluation as described was carried out using the bacterium, Pseudomonas aeruginosa. The composition tested was a mixture of 2-methyl-4,5-trimethylene-4-isothiazolin-3-one and a 2:1 complex of 2-mercaptopyridine-1-oxide with zinc.

An isobologram was drawn utilising concentrations of 0, 11, 22, 33, 45, 56, 67, 78, 89 and 100 microgram $cm^{-3}$ of the complex and 0, 11, 22, 33, 45, 56, 67, 78, 89 and 100 microgram $cm^{-3}$ of the isothiazolinone.

From the results obtained, it was found that the lowest sum of the fractional inhibitory concentration (FIC) was 0.4 which was achieved with a mixture containing 11 microgram $cm^{-3}$ of the complex and 22 microgram $cm^{-3}$ of the 2-methyl-4,5-trimethylene-4-isothiazolin-3-one. This may be contrasted with the minimum inhibitory concentrations (MIC) of the two individual components against the same micro-organism in the same experiment which were found to be 78 microgram $cm^{-3}$ and 100 microgram $cm^{-3}$, respectively.

I claim:

1. A composition having an FIC value less than one which comprises
   a) a 4,5-polymethylene-4-isothiazolin-3-one or a salt thereof, and
   b) a complex of 2-mercaptopyridine-1-oxide with a metal of Group (II)B.

2. The composition of claim 1 wherein a) is a compound of formula

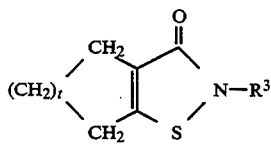

wherein t is 1 or 2, and $R^3$ is hydrogen or linear or branched alkyl having up to 12 carbon atoms.

3. The composition of claim 1 wherein component a) is either 4,5-trimethylene-4-isothiazolin-3-one or 2-methyl 4,5-trimethylene-4-isothiazolin-3-one.

4. The composition of claim 1 wherein component b) is a 2:1 complex of 2-mercaptopyridine-1-oxide and zinc.

5. The composition of claim 1 which comprises 2-methyl-4,5-trimethylene-4-isothiazolin-3-one and a 2:1 complex of 2-mercaptopyridine-1-oxide and zinc.

6. The composition of claim 1 which contains components (a) and (b) in the proportions by weight of from 100:1 to 1:100.

7. The composition of claim 1 wherein the sum of the fractional inhibitory concentration of the components is less than 0.7.

8. A medium which is susceptible to attack by microorganisms and which contains from 0.0001 to 10% by weight of the medium of a composition comprising
   a) a 4,5-polymethylene-4-isothiazolin-3-one or a salt thereof, and
   b) a metal complex of 2-mercaptopyridine-1-oxide with a metal of Group (II)B.

9. A medium as claimed claim 8 which is a cosmetic.

10. A method for inhibiting the growth of microorganisms on, or in, a medium, which comprises treating the medium with a composition comprising
    a) a 4,5-polymethylene-4-isothiazolin-3-one or a salt thereof, and
    b) a metal complex of 2-mercaptopyridine-1-oxide with a metal of Group (II)B.

11. A composition according to claim 1 wherein the metal of Group (II)B is zinc.

12. A medium according to claim 8 wherein the metal of Group (II)B is zinc.

13. A method according to claim 10 wherein the metal of Group (II)B is zinc.

* * * * *